United States Patent [19]
Lau et al.

[11] Patent Number: 5,173,303
[45] Date of Patent: Dec. 22, 1992

[54] CUTANEOUS DELIVERY OF ORGANIC MATERIALS

[75] Inventors: John R. Lau; Blair Geho, both of Wooster; Darryl H. Woods, Dalton, all of Ohio

[73] Assignee: Technology Unlimited, Inc., Wooster, Ohio

[21] Appl. No.: 726,037

[22] Filed: Jul. 5, 1991

Related U.S. Application Data

[63] Continuation-in-part of Ser. No. 356,506, May 25, 1989, abandoned.

[51] Int. Cl.$^5$ .................. A61K 37/22; A01N 25/28
[52] U.S. Cl. ........................ 424/450; 424/405; 514/918
[58] Field of Search ............... 424/450; 514/918, 962, 514/963, 964, 965, 919

[56] References Cited

U.S. PATENT DOCUMENTS

| | | | |
|---|---|---|---|
| 4,855,090 | 8/1989 | Wallach | 264/4.1 |
| 4,942,036 | 7/1990 | Geho et al. | 424/425 |
| 5,006,343 | 4/1991 | Benoon et al. | 424/450 |

Primary Examiner—Thurman K. Page
Assistant Examiner—Neil Levy
Attorney, Agent, or Firm—Ray S. Pyle

[57] ABSTRACT

This invention discloses the phenomenon of physically sequestering organic soluble material by lamellar envelopment. It is to be distinguished from microdroplets of water insoluble drugs coated with a phospholipid prepared by sonication. Actual reduction to practice in a commercial effort has been with insect repellent. Hence, the disclosure will refer essentially to the dispersing of DEET.

5 Claims, 1 Drawing Sheet

CUTANEOUS DELIVERY OF ORGANIC MATERIALS

CROSS REFERENCE TO RELATED APPLICATIONS

This application is a continuation-in-part of prior application Ser. No. 356,506, filed May 25, 1989 now abandoned. The subject matter of said application Ser. No. 356,506, is incorporated by reference into the present application.

BACKGROUND OF THE INVENTION

1. Field of the Invention

Liposomes can be formed from phospholipid molecules that are not very soluble in aqueous media but are soluble in organic solvents A species of the field is the establishment of a liposomal delivery system that anchors aromatic hydrocarbon derivatives, such as mosquito repellents and insecticides, to the stratum corneum of a warm blooded host.

"Liposome" and "vesicle" may be used interchangeably herein because the art is not sufficiently exact with respect to the parameters of nomenclature.

2 Description of Prior Art

Liposomes are known to encapsulate water soluble pharmacological agents in their core volume. Thus, these agents are separated in minute particles from the surrounding media The liposomes have potential for site specific delivery, as known in the prior art, for their use as carriers to enhance therapeutic and protective indices.

The prior art method of making vesicles, or liposomes, is to subject a mixture of amphipatic phospholipid, such as egg lecithin, and an aqueous solution of the intended burden to high energy output, such as sonication or microfluidization. The amphipatic lipid breaks into smaller units which form bladders known as vesicles or liposomes. In the process, some of the aqueous medium is captured in the core volume of the liposomes.

This basic known system, as described, is satisfactory for aqueous media but is inoperative for organic molecules that are minimally soluble in aqueous media.

This invention distinguishes over all known prior art, including intensive literature studies, by the discovery that formation of amphipatic lipids into vesicles in the presence of organic molecules that are minimally soluble in aqueous media exhibit a phenomenon of sequester by lamellar liposomal entrapment of the organic substance in the manner illustrated in the drawing. The organic substance would not ordinarily be expected to fill the aqueous core volume of a vesicle/liposome during formation. The outermost portion of a bipolar lipid membrane, both on the exterior surface and on the core volume wall, is a hydrophilic sphere. Therefore, it is generally accepted as fact that an organic substance would not be encapsulated.

It is an object of this invention to provide a slow release delivery system for chemicals which are soluble in an organic solvent, and not water soluble, by capture of such chemicals in a bipolar lipid vesicle. This object is carried out by lamellar envelopment.

Another object of the invention is to provide an anchor molecule for such sequestered agent, the anchor molecule being selected to have affinity for the desired host surface under consideration. The primary target surface of the preferred embodiment is the stratum corneum. Stratum corneum is defined in *Tabor's Cyclopedic Medical Dictionary*, Edition 14 (F. A. Davis Company) as the outermost horny layer of the epidermis.

SUMMARY OF THE INVENTION

The term "burden," as used herein, shall refer in general to a substantially water insoluble, biologically active, aromatic, liquid, organic hydrocarbon derivative for application to a living host skin surface to elicit a desired response. It may be, for example, an enhancement chemical, an insect repellent, or a cosmetic such as perfume. Normally a sunscreen is water-soluble, but some fit the description.

The burden is sequestered by lamellar envelopment in a bipolar lipid liposome in the special sense of this invention.

Application of an environment enhancement chemical to the skin of a warm blooded host is accomplished by liposomal sequestration of the enhancement chemical through lamellar envelopment and by anchoring the liposome to the stratum corneum. Anchoring is done by means of a molecule having a lipophilic moiety engaged onto the liposome and having a moiety with affinity for the stratum corneum.

Specific examples of a burden material are molecules such as 6,12(2-Ethyl-1,3,-hexanediol) and N,N-Diethyl-m-toluamide (DEET). Flea and tick repellents and/or water insoluble insecticides are further examples.

The drawing illustrating this invention shows the discovered unique sequestering of the described class of water insoluble burden by lamellar envelopment. Liposomes cannot be formed in a organic solvent, and water insoluble chemicals cannot be trapped in an aqueous core volume of a lipid vesicle. This invention discloses the phenomenon of physically sequestering liquid organic substances, which are volatile at ambient temperature and pressure, by lamellar envelopment. It is to be distinguished from microdroplets of water insoluble drugs coated with a phospholipid prepared by sonication.

Then, by attaching an anchor molecule, an article of manufacture is produced which will attach to a skin cell. By anchoring to the human stratum corneum with sodium pyridinethione, the sequestered burden will remain in place as it gradually escapes its sequestering lipid and functions for an extended period of time.

The anchor concept differs from prior art targeting in that a "target" of the prior art travels with a liposome to seek out an elusive target area or organ. The discovery that makes this invention so outstandingly effective is that when the combination of lamellar lipid, burden, and anchor is applied to the epidermis, it is placed on the cell to which it develops an anchored relationship.

To understand this invention, it is well to understand what it is not. It is not entrapment within a lipid vesicle aqueous core volume as is now well known in the art, nor a coating of polar lipid on microdroplets.

This invention is an envelopment phenomenon. The liposomal phospholipid lamellar membrane functions as the enveloper or as a wrapper of sequestered burden.

DEET, which is a liquid organic substance volatile at ambient temperature and pressure, and substantially insoluble in water but soluble in organic solvents, is captured in accordance with this invention by lipid lamellar envelopment resulting in sequestration in a bipolar lipid membrane.

DEFINITION

Figure 1:
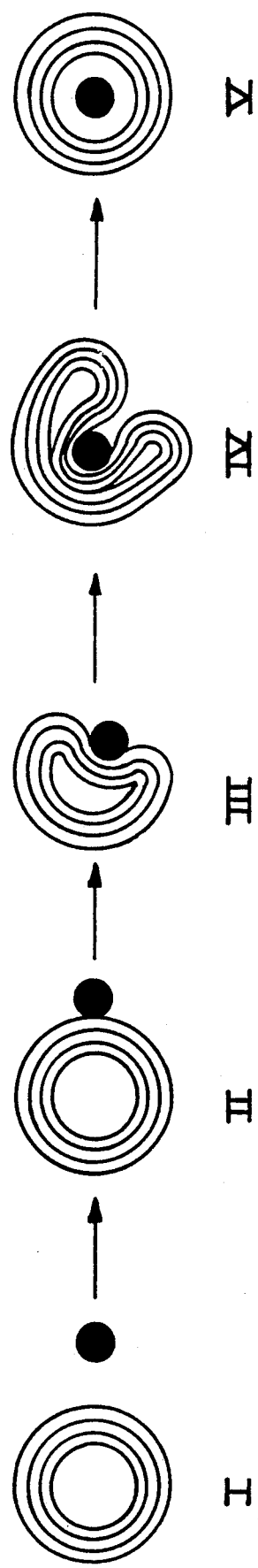
FIG. 1 is a series in the process of an organic particle being enveloped and sequestered as if wrapped by a liposomal lamellae structure.

Because the invention is a unique means for dispensing a biologically active substance, such as an insect repellent or insecticide, and is not in the substance per se, reference hereinafter for disclosure will generally be to "insect repellent" for economy of expression and shall include any burden which is insoluble in water but soluble in organic solvents, and is volatile at ambient temperature and pressure. Further examples include, but are not limited to, perfume and organic substances which relieve the pain resulting from burns. Lipid-based sunscreens are examples of substances which can be used to prevent sunburn.

An amphipatic lipid has one moiety which is hydrophilic and an opposing lipophilic moiety.

A liposome (or a vesicle) is a result of the application of energy to a mix of water or a water solution and an amphipatic lipid which forms into bladders. A portion of the water is captured in the core volume of a liposome as it is formed.

The term "envelop" or "wrap" resulting in sequestration by liposomal lamellae is a concise statement of the engulfment phenomenon discovered according to this invention. To engulf is to swallow up. This invention is in the discovery that a water insoluble substance can be enveloped, wrapped, or engulfed by a lamellar lipid in what has heretofore been considered a hostile environment.

"Encapsulate," as used herein, is limited to a very specific meaning which is fully developed in the disclosure of this document. The term excludes core volume entrapment.

"Bio-organic" and "biologically active" and "aromatic hydrocarbon" shall refer to an organic substance, practically insoluble in water, effective to repel or kill insects, and shall include those organics which will be useful for treating skin for relief of pain as well as enhancement chemicals such as perfumes and sunscreens.

DETAILED DESCRIPTION

One preferred embodiment of the invention is to provide an article of manufacture for repelling or killing insects comprising a substantially water insoluble organic compound, N,N diethyl-m-toluamide, known as "DEET," or an organic soluble pesticide loaded to a bipolar lipid body. According to this invention, a targeting molecule for anchoring the lipid body has a moiety exhibiting affinity for lipid structures and thereby united to the lipid body, and an anchor moiety having affinity for the stratum corneum.

The procedure used for making the product as tested is set forth below:

1. 120 mg of the sodium salt of pyridinethione is dissolved in 525 ml of deionized water and allowed to stir at ambient temperature for 15 minutes.

2. 120 g of hydroxylated lecithin is weighed into an 800 ml beaker while 525 ml of solubilized sodium pyridinethione is added in 100 ml aliquots. During pyridinethione addition, the same is slowly polytroned with an ultra-Turrax TP-18/1051 Polytrone from Janke and Kunkel IKA Laboratory, at setting #4, for 15 minutes.

3. After the lecithin had been mixed, 180 ml of 100% diethyl-m-toluamide (DEET) was added to the 600 ml of sodium pyridinethione lecithin solution in three aliquots of 60 ml each, five minutes apart. After the last aliquot, the total volume of 825 ml was allowed to mix while polytroning on setting #4 for 10 minutes. Then, 495 of deionized water was added and allowed to mix while polytroning on setting #4 for 30 minutes. The total volume of the solution at this point was 1320 ml.

4. The 1,320 ml of the pyridinethione-lecithin-DEET suspension was processed through the microfluidizer at a head pressure of 20 psig and a shear pressure of 2,500 psig. The total recoverable volume of 1,320 ml was recycled three time through the microfluidizer under the above conditions. The initial starting temperature of the suspension was 20 degrees C., and the final temperature following microfluidization was 63 degrees C.

The DEET molecule possesses hydrophobic (lipid seeking) groups such as the ethyl moiety and the meta methylbenzene rings. The DEET molecule is enveloped by a large multi-lamellar liposome. The capture and sequestration of the DEET molecule is illustrated in the five-step illustration in FIG. 1, which are reproductions of actual images from electron microscopy. The small black spot represents a particle of DEET, and the multilamellar rings represent a larger liposome.

The liposome, no longer being intact, is simply a large multilamellar array of lipid which seeks to repair itself thermodynamically, and in so doing, sequesters by lamellar envelopment the DEET particle or molecule by surrounding the DEET with the large multilamellar array of preformed bipolar phospholipid membrane. The DEET particle thus has been sequestered and protected by the lipid.

The liposomal membrane with the sequestered DEET has the following properties: It breaks upon freezing and warming causing the DEET to coalesce into a larger separate phase. The liposomal lamellae are acting as an enveloping agent. The major portion of the lamellae evidence a distorted nonspherical pattern, as illustrated in FIG. 1.

The sequestering agent has lamellae, or onion skin kinds of structures, which have been preformed in a single step. A multiple protective layer pattern has been developed that will sequester the DEET.

The described liposomal system has captured or sequestered DEET in a new way. It has been shown that once the DEET has been sequestered by the lamellae, its escape into the atmosphere is restricted and slowed. This concept forms the basis for timed release of water insoluble substances such a DEET and prolongs their duration of action.

It has been discovered that the above-described article of manufacture may be employed in the described state and can cling to skin and hair for a period of time without the anchor.

To enhance the usefulness of the article, an anchor has been developed. The molecule sodium pyridinethione, has a moiety that is lipophilic and a moiety that has affinity for stratum corneum.

If mixed as a water solution, and used as a water phase in forming classical liposomes or vesicles, the pyridinethione simply exists in the solution until liposomes are formed, and then the lipid moiety of the pyridinethione attaches to the lipid wall of the liposome. In order to be certain that one being edified by this specification understands the role of pyridinethione, it is emphasized that fully formed liposomes with encapsulated DEET, will cling to hair and skin cells to some degree.

However, the preferred procedure set forth above as a fourth step procedure is the actual reduction to practice and remains the preferred embodiment.

Thereafter, a quantity of the final mix, when applied to the skin of a host, will attach to the dead skin cells and anchor the article to the skin, but will be lost when the cells to which they are anchored slough off in the natural course. The loss rate of skin cells controls the time of effectiveness. The carrier is not permanent but will be self-removed in about the time it is no longer effective. This molecule is the preferred embodiment of a liposome agent and is the best mode selection.

EXAMPLES OF TOPICAL REPELLENT APPLICATIONS

1. Superior Insect Repellency

The preferred embodiment with the insect repellent DEET as the repellent active material, has been compared with other commercially available repellent products. In the test described herein, the preferred embodiment contained 13.6% of the active material, while the two comparison products contained 25% DEET.

The products were tested under carefully controlled test conditions with human volunteers in the Everglades in Florida. Each subject tested all three products simultaneously (using each arm and a leg for the test sites). The object of the test was to determine the length of time until repellency was lost, as evidenced by two consecutive bites in a thirty minute period of time. Each product was tested sixteen times.

| | RESULTS | | |
|---|---|---|---|
| | PREFERRED EMBODIMENT 13.6% | COMPARISON PRODUCT #1 25.0% | COMPARISON PRODUCT #2 25.0% |
| TIME OF PROTECTION (HOURS ± S.D.) | 4.65 ± 1.37 | 3.03 ± 2.68 | 3.40 ± 1.64 |

The preferred embodiment gave significantly more protection from the insect bites than did two commercial products at almost twice the level of the same insect repellent, DEET.

2. Preferred Embodiment Provides Less Skin Absorption and a Higher Skin Level of Active Material The preferred embodiment was compared to DEET alone on the skin to determine the ability of the preferred embodiment to maintain a higher skin level of the DEET, and to protect the body from absorbing the DEET, as measured by urine levels of DEET. In this study, radio-labelled $^{14}$C-DEET was used for determining the presence of DEET on the skin or in the urine.

The test animals were adult Lewis rats with shaved backs. The test materials (preferred embodiment containing DEET, and DEET alone in isopropyl alcohol) both at 13.6% DEET, were applied to the backs of rats. The rats were individually caged in metabolic cages to collect the urine and to prevent the rats from licking the backs of other rats. After 16 hours, the skin of the rats was removed, and the amount of DEET present was measured. At the same time, the DEET was measured in the collected urine samples.

| RESULTS | | |
|---|---|---|
| | PERCENT OF APPLIED DEET ± S.D. | |
| PRODUCT TESTED | SKIN | URINE |
| PREFERRED EMBODIMENT | 25.4 ± 5.7 | 21.9 ± 3.8 |
| DEET IN ALCOHOL | 18.6 ± 3.9 | 32.0 ± 4.0 |

The preferred embodiment was successful in maintaining a higher level of DEET and in preventing skin absorption of the DEET.

What is claimed is:

1. An article of manufacture, comprising:
    an insect repellent which is substantially insoluble in water and soluble in organic solvents;
    a first phase which is a liposome lamellae enveloping a second phase which is a bio-organic insect repellent soluble in organic solvents and substantially insoluble in water; and
    an anchoring molecule of sodium pyridinethione having a moiety embedded in said liposome.

2. A protective structure for stratum corneum, comprising a liposome and a burden of substance selected from the class consisting of insect repellents, insecticides, burn medication, and sunscreen, and an anchor molecule having a first moiety anchored to the vesicle, and a second moiety that has the potential to anchor to the stratum corneum when applied thereto.

3. A lamellae sequestered burden of claim 2, with anchor molecules having a lipophilic moiety engaged with the membrane structure and a moiety attracted to stratum corneum.

4. An article of manufacture comprising:
    an insect repellent which is substantially insoluble in water and soluble in organic solvents;
    a first phase which is a liposome lamellae enveloping a second phase which is 6,12(2-Ethyl-1-3)hexanediol insect repellent soluble in organic solvents and substantially insoluble in water; and,
    an anchor molecule of sodium pyridinethione having a moiety embedded in said liposome.

5. An article of manufacture comprising:
    an insect repellent which is substantially insoluble in water and soluble in organic solvents;
    a first phase which is a liposome lamellae enveloping a second phase which is N,N,Diethyl-M-toluamide insect repellent soluble in organic solvents and substantially insoluble in water; and,
    an anchor molecule of sodium pyridinethione having a moiety embedded in said liposome.

* * * * *